United States Patent [19]

Fischer

[11] Plant 4,935

[45] Nov. 9, 1982

[54] AFRICAN VIOLET NAMED FAIRY QUEEN

[75] Inventor: Arnold W. Fischer, Hanover, Fed. Rep. of Germany

[73] Assignee: Pan-American Plant Company, Parrish, Fla.

[21] Appl. No.: 252,615

[22] Filed: Apr. 9, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new and distinct African Violet plant characterized by its profuse production of white flowers, the petals of which have a bright pink, ruffled edge which gives the plant a very striking appearance. This plant has a vigorous growth habit, a compact rosette shape and abundant medium green foliage which provides an exotic color combination when the plant is in full bloom.

3 Drawing Figures

BACKGROUND OF THE NEW PLANT

This new African Violet plant originated as a seedling of unknown parentage growing among a field of violet plants maintained at Fallbrook, Calif., for the production of new and exotic African Violet varieties. This new plant was discovered by me at Fallbrook, Calif., in 1977 and its unique and delightful flowers prompted me to select this plant for propagation and test. I reproduced the discovery plant, by means of cuttings, at Fallbrook with very favorable results and subsequently propagated the plant through several successive generations, which demonstrated that the novel characteristics of this plant would hold true from generation to generation and appeared to be firmly fixed. This new violet plant is now being propagated on a commercial scale by means of cuttings at West Chicago, Ill., and at Parrish, Fla.

DESCRIPTION OF THE DRAWINGS

This new violet plant is illustrated by the accompanying drawings, of which sheet 1 is a full color photographic view of a potted plant in full bloom, and sheets 2 and 3 are prints of machine copies of the front and back sides, respectively, of typical leaves of this plant.

DESCRIPTION OF THE NEW PLANT

The following is a detailed description of my new African Violet plant based upon observations made in greenhouse at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—*Saintpaulia ionantha.*
- *Commercial.*—African Violet.

Form: Compact and of rosette shape.
Growth: Vigorous and strong.
Growth rate: Vigorous and rapid.
Foliage:
- *Quantity.*—Abundant, with about 26 leaves.

- *Size of leaf.*—Length — From insignificant to about 80 mm. Width — From insignificant to about 80 mm.
- *Shape of leaf.*—Reniform, with rounded tip and truncate base, and with wavy or sinuate margins which tend to curl under.
- *Texture.*—Pubescent.
- *Appearance.*—Glossy.
- *Color.*—Upper side — 137B. Under side — 138D.
- *Ribs and veins.*—Pinnate.
- *Rachis.*—Up to 90 mm. long.
- *Petioles.*—Length — Up to 65 mm.

THE BUD

Form: Globular.
Size: The size varies in both diameter and length.
Rate of opening: Typical violet.
Color of petals:
- *When sepals first divide.*—144D.
- *When petals begin to unfurl.*—155D for the petal body and 64D for the petal edge.

Sepals:
- *Number.*—Five.
- *Shape.*—Lanceolate and branched, becoming flat when the flowers open.
- *Color.*—Inside — 144C. Outside — 144B.
- *Striae.*—None.

Calyx:
- *Size.*—Small.
- *Shape.*—Calyx splits to star shape.
- *Aspect.*—Hairy.

Peduncle:
- *Character.*—Rigid and erect.
- *Length.*—From insignificant to about 74 mm.
- *Aspect.*—Hairy.
- *Color.*—144B.

THE FLOWER

Blooming habit: Intermittent.
Flowering: Profusely.
Flower size: Medium.
- *Diameter.*—About 30 to 400 m.
- *Depth.*—Flat.
- *Borne.*—As a cyme.
- *Shape.*—Cup-shaped when bloom first opens, becoming flat when bloom matures.

Petalage:

*Number of petals.*—Five.

*Arrangement.*—Sympetalous.

*Form.*—Rotate-zygomorphic with rounded apex and sinuate margin.

*Texture.*—Soft.

*Appearance.*—Satiny.

*Color.*—Outer petals: Body — White 155D. Margins — Pink 64A. Inside petals: Body — White 155D. Margins — Pink 64D.

Petaloids: None.

Flower stem:

*Character.*—Strong and upright.

*Length.*—From insignificant to about 74 mm.

*Color.*—144B.

Persistence: The flowers hang on and dry.

Fragrance: None.

Lasting quality:

*On plant.*—10 to 20 days.

REPRODUCTIVE ORGANS

Stamens:

*Anthers.*—Number: Two. Arrangement: Monadelphous. Size: About 3 mm. square. Color: Whitish yellow. Pollen: Color — Yellow.

Pistils:

*Number.*—One.

*Style.*—Length: About 5 mm. Color: White to pink.

*Stigma.*—Color — White.

Ovaries: Hypogynous and tomentose.

This new African Violet cultivar is particularly distinguished by its white zygomorphic flowers, the petals of which have a bright pink ruffled edge which provides a very striking appearance. These flowers keep very well and are of good substance and the unique foliage has a wavy or ruffled edge which provides a very distinctive character for the blooming plant.

I claim:

1. A new African Violet plant, substantially as herein shown and described, characterized by its profuse production of white flowers, the petals of which are bordered by a narrow pink and ruffled edge. The plant has a vigorous growth habit with abundant foliage which has a unique wavy or ruffled margin.

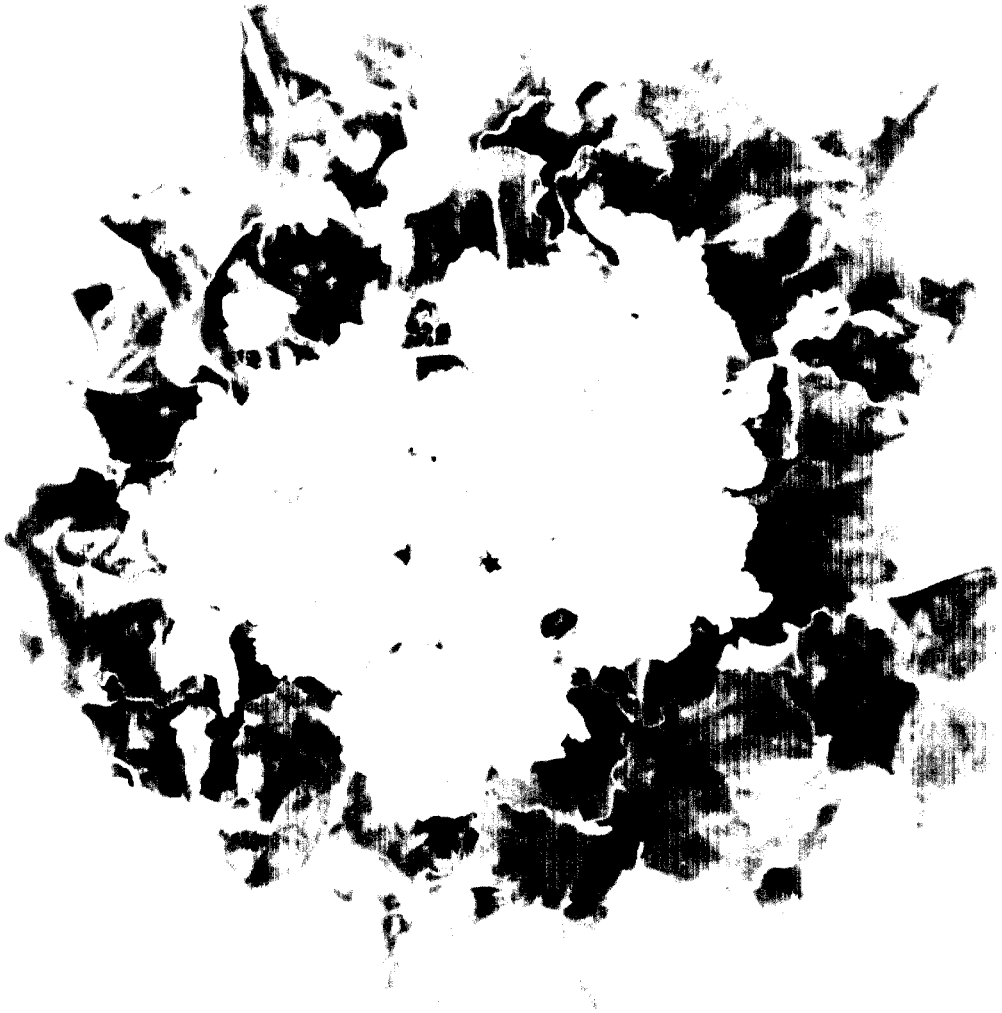

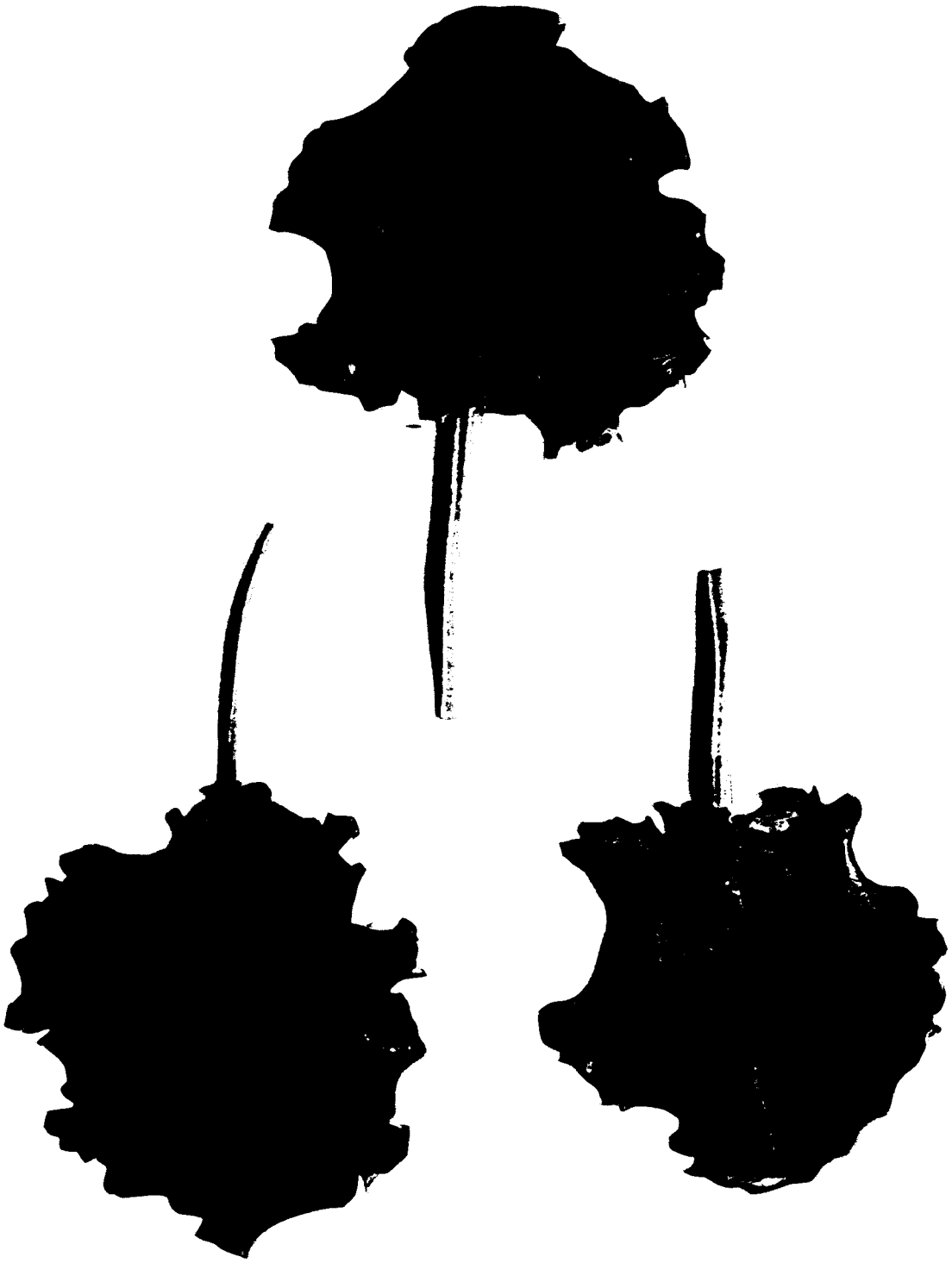

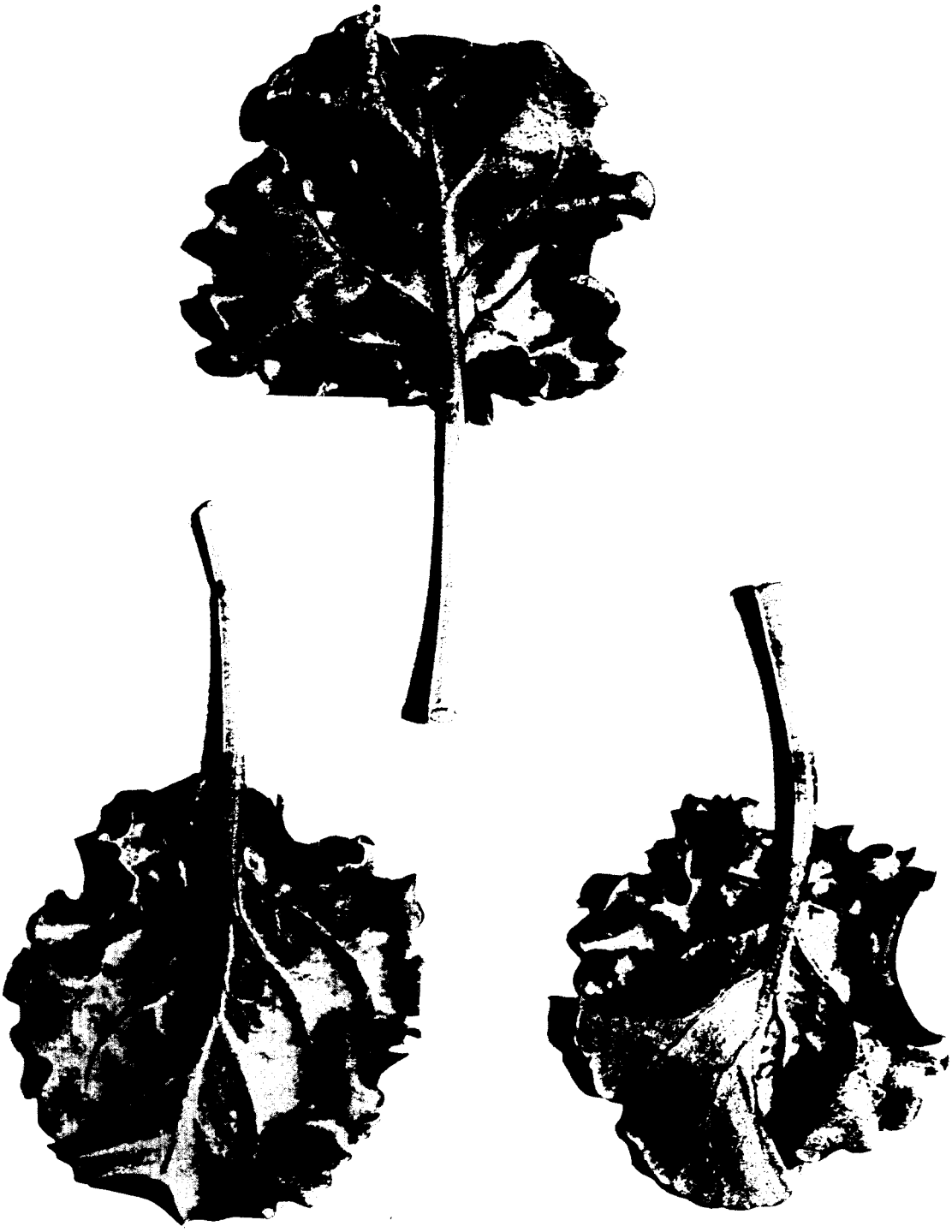

* * * * *